United States Patent [19]

Schiff et al.

[11] Patent Number: 4,765,961
[45] Date of Patent: Aug. 23, 1988

[54] APPARATUS FOR DETECTION OF CERTAIN NITROGEN-CONTAINING GASES USING CHEMILUMINESCENCE

[75] Inventors: Harold I. Schiff, Toronto, Canada; Donald H. Stedman, Englewood, Colo.

[73] Assignees: The University of Michigan, Ann Arbor, Mich.; Scintrex Limited, Concord, Canada

[21] Appl. No.: 605,599

[22] Filed: Apr. 30, 1984

[51] Int. Cl.$^4$ ...................... G01N 21/76; G01N 21/77
[52] U.S. Cl. ......................................... 422/52; 422/86; 422/87; 422/91; 436/116; 436/118; 436/169; 436/172; 435/8
[58] Field of Search ...................... 422/52, 86, 87, 91; 436/56, 110, 116–118, 52, 135, 172, 169; 435/8

[56] References Cited

U.S. PATENT DOCUMENTS

| | | | |
|---|---|---|---|
| 3,659,100 | 4/1972 | Anderson et al. | 250/71 R |
| 3,690,832 | 9/1972 | Plakas | 23/230 B |
| 3,700,896 | 10/1972 | Anderson et al. | 250/71 R |
| 3,712,793 | 1/1973 | Lyshkow | 23/232 E |
| 3,881,869 | 5/1975 | Neti et al. | 422/52 |
| 3,923,462 | 12/1975 | Cavanagh | 422/52 |
| 3,940,250 | 2/1976 | Plakas et al. | 23/230 B |
| 4,013,418 | 3/1977 | Plakas | 422/52 |
| 4,229,593 | 11/1981 | Dopp | 436/164 |
| 4,287,306 | 9/1981 | Brewer | 435/801 |
| 4,410,493 | 10/1983 | Joslyn | 422/56 |
| 4,518,566 | 5/1985 | Sorensen | 422/88 |
| 4,588,555 | 5/1986 | Provonchee | 436/169 |

OTHER PUBLICATIONS

Seitz, W. R. and Hercules, D. M., "Chemiluminescent Analysis for Trace Elements", *Chemiluminescense and Bioluminescense*, edited by Cormier et al., 427–449 (New York: Plenum Press, 1973).
Kok et al., *Environ. Sci. Technol.*, vol. 12, No. 9, p. 1072 (1978).
Maeda et al., *Anal. Chem.*, vol. 53, No. 2, p. 307 (1980).
Levaggi et al., *Environ Sci. Technol.*, vol. 8, No. 4, p. 348 (1974).

Primary Examiner—Barry S. Richman
Assistant Examiner—Lynn M. Kummert
Attorney, Agent, or Firm—Rohm & Monsanto

[57] ABSTRACT

Chemiluminescence is detected in a luminol solution free of metal ions flowing through a porous material to indicate the presence of certain nitrogen-containing gases. Continuous monitoring of atmospheric gases is possible through use of the described methods and related apparatus.

9 Claims, 4 Drawing Sheets

APPARATUS FOR DETECTION OF CERTAIN NITROGEN-CONTAINING GASES USING CHEMILUMINESCENCE

BACKGROUND OF THE INVENTION

This invention relates to improvements in the detection of certain nitrogen-containing gases using chemiluminescence.

Chemiluminescence is the emission of light that results from a chemical reaction. A chemical reaction between substances generally is accompanied by the release of energy. Frequently this energy is manifested in the form of heat. Occasionally, however, it is accompanied by the production of light in the visible or infrared portion of the spectrum.

The detection of chemilum inescence when two substances are brought together can serve as a method for detection and analysis of one of the substances. For example, the occurrence of chemiluminescence when substance "B" is added to substance "A" may provide evidence of the presence of substance "A", while the intensity of the chemiluminescence may provide information on the amount of "A" present. There is, for example, a commercially available instrument that operates on this principle and which determines the concentration of nitric oxide (NO) from the chemiluminescence produced when it reacts with ozone.

A difficulty frequently encountered with chemiluminescence as a method for chemical analysis is its lack of specificity. Substances other than substance "A" also may produce chemiluminescence in the presence of substance "B". Although the wavelengths of the emitted light are characteristic of the particular chemical reaction, the range of wavelengths involved may overlap wavelengths emitted from reactions involving chemiluminescence between substance "B" and other interfering substances. In such cases the interfering substances first must be removed before the analysis is performed.

Luminol (5-amino-2,3-dihydro-1,4-phthalazine dione) is known to chemiluminesce with a number of oxidizing agents in alkaline solution when metal ion catalysts are provided (White, E. H. in "Light and Life" 1st Edition McElroy, W. D., Glass, B. Eds.; Johns Hopkins Press: Baltimore, 1962, p. 183). This technique has been used to measure hydrogen peroxide ($H_2O_2$) as well as other oxidizers produced by biological systems (Selz, W. R. Methods Enzym. 1978, 57, 445, Schroeder, H. R. et al Methods Enzym. 1978, 57, 425) and to measure metal ion concentrations when excess $H_2O_2$ is added (Seitz, W. R.; Hercules, D. M. in "Chemiluminescence and Bioluminescence"; Cormier, M. J., Hercules, D. M., Lee, J. Eds; Plenum Press, New York p. 427). Kok et al (Environ. Sci. Tech. 1978, 12, 1072; 1978, 12, 1077) devised a system for measuring $H_2O_2$ based on the $H_2O_2$/luminol/metal ion reaction. All of these reactions involving chemiluminescence occur in the liquid phase and depend upon the presence of metal ion catalysts in the solution.

Anderson et al (U.S. Pat. No. 3,659,100, August 1970 and U.S. Pat. No. 3,700,896, October 1972) described a system based on luminol/$H_2O_2$ chemiluminescence with the catalyst being a gas in equilibrium with the luminol solution instead of a metal ion. Anderson et al further disclosed that the system can be used as a detector of $NO_2$, $O_3$ and $SO_2$ by using various inlet traps to distinguish between these gases.

Maeda et al (Anal. Chem. 1980, 52, 307) described the development of a detector for nitrogen dioxide ($NO_2$) based on the reaction involving chemiluminescence between $NO_2$ and luminol. Metal ions were carefully removed from the solution eliminating interferences encountered with other oxidants which required the presence of metal ion catalysts.

The chemiluminescence between $NO_2$ and luminol is a process which occurs on the surface of the liquid. This is in contrast with chemiluminescence involving other oxidants, such as $H_2O_2$, which occur from reaction in the bulk phase of the liquid. Maeda et al described in the aforementioned publication a reactor in which the gas was drawn over the surface of a pool of luminol solution. A photomultiplier was located close to the surface of the pool and monitored the intensity of the chemiluminescence. This Maeda reactor design has two serious drawbacks. It is very sensitive to both, movement during sampling and positioning of the cell, to keep it level. Any wetting of the wall of the reactor above the pool leads to changing surface volume and changing signal. In addition, this design exhibited a slow response to changes in concentration of $NO_2$.

SUMMARY OF THE INVENTION

In accordance with the instant invention, the aforementioned problems of the Maeda reactor design are overcome by providing a porous material through which the luminol solution flows.

Various aspects of the invention are as follows:

A method for detecting the presence of nitrogen gases in a gas sample which comprises flowing a luminol solution free from metal ions through a porous material, contacting said luminol solution with said gas sample as said luminol solution flows through said gas sample and detecting chemiluminescence resulting from chemical reaction between said nitrogen gases and said luminol solution.

Apparatus for detecting the presence of and measuring nitrogen gases in a gas sample comprising a porous material having a luminol solution free from metal ions flowing therethrough in the presence of said gas sample and photomultiplier means for detecting and measuring chemiluminescence in said luminol solution.

BRIEF DESCRIPTION OF THE DRAWINGS

This invention will become more apparent from the following detailed description, taken in conjunction with the appended drawings, in which.

DETAILED DESCRIPTION OF THE INVENTION INCLUDING THE PREFERRED EMBODIMENT

Generally speaking, in the practice of the present invention an alkaline luminol solution free from metal ions is permitted to flow through any suitable porous material such as, for example, glass frit, cellulose fibre or glass fibre filter "paper".

The employment of a porous material promotes surface reaction and minimizes bulk liquid reaction by providing a high surface-to-volume ratio. The filter paper is viewed by a photomultiplier. The gas sample, e.g., air, is forced to pass between the front of the photomultiplier and the filter paper reaction region. The luminol solution is permitted to flow through and along the filter paper bringing fresh luminol into contact with the gas sample and washing away the products of the chemical reaction.

The signal obtained with such apparatus and as a result of the chemiluminescence has been found to be insensitive to movement and placement and to exhibit a fast response time. With respect to the latter, the apparatus embodying the invention was able to follow a modulation up to 2 Hz of 20 parts per billion (ppbv) of $NO_2$ with no loss of signal. In this embodiment, a sensitivity to 5 parts per trillion (pptv) of $NO_2$ has been demonstrated.

Figure 1:
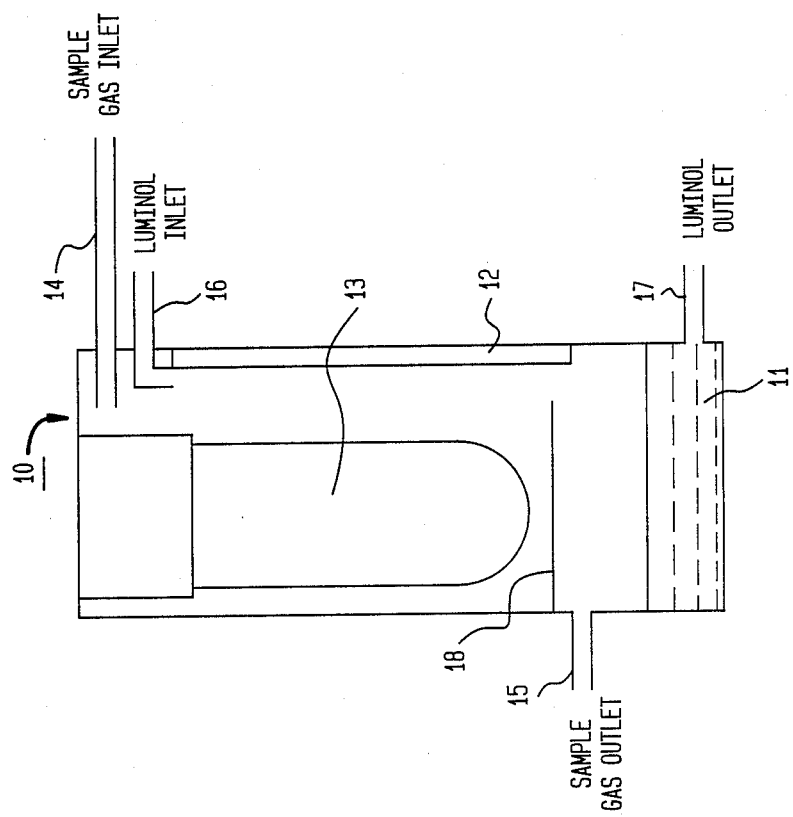
FIG. 1 is a schematic representation of one form of apparatus embodying, and that may be used in practising, the present invention.

In the embodiment of the invention shown in FIG. 1 there is a housing 10 containing a reservoir 11 for luminol solution, a strip of porous material in the form of filter paper 12 extending part way down one side of housing 10, and a photomultiplier 13 mounted to detect chemiluminescence from luminol-impregnated filter paper 12. Gas to be tested enters the interior of housing 10 via a tube 14 and exits from housing 10 via a tube 15 after passing over the luminol-impregnated filter paper 12. Any suitable pump for the gas to be tested may be used to cause the gas to flow through housing 10. The luminol solution is introduced into housing 10 via an inlet tube 16 and is removed from reservoir 11 via an outlet tube 17.

A shield 18 below photomultiplier 13 and above the surface of the luminol solution in reservoir 11 prevents any chemiluminescence at the surface of the luminol solution in reservoir 11 from being detected by photomultiplier 13.

Figure 2:
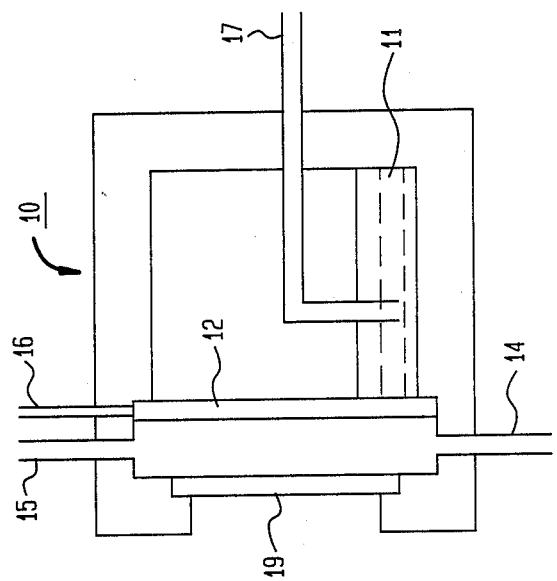
FIG. 2 is a schematic representation of another form of apparatus embodying, and that may be used in practising, the present invention.

The embodiment of FIG. 2 is similar to that of FIG. 1 except that the gas to be tested passes between a glass window 19 and porous material 12 in the form of glass frit, and the photomultiplier (not shown), is located outside of housing 10 adjacent window 19.

In operation the luminol solution is supplied continuously to the top of porous material 12, flows through porous material 12, and the excess drips off the bottom of porous material 12 into reservoir 11, which is outside the viewing region of photomultiplier 13. A small pump (not shown) returns the luminol solution to the top of porous material 12.

Figure 3:
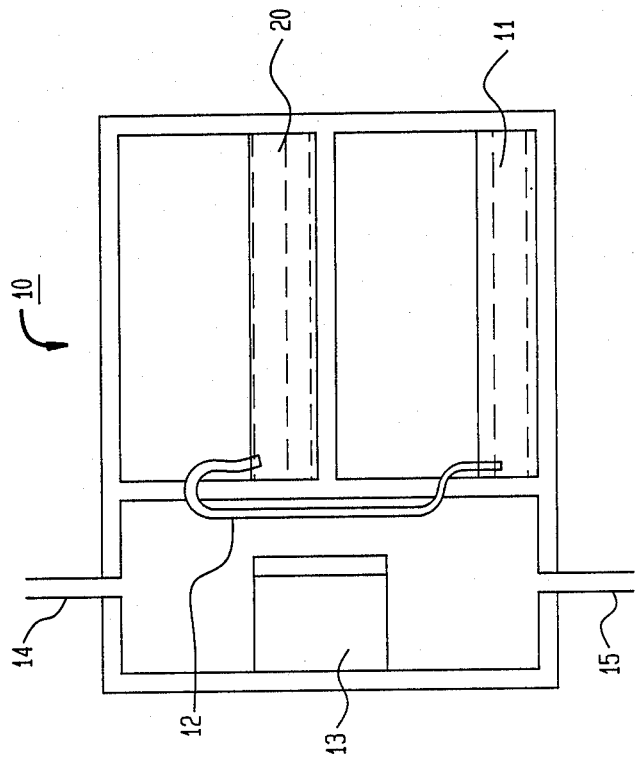
FIG. 3 is a schematic representation of yet another form of apparatus embodying, and that may be used in practising, the present invention.

In the preferred embodiment shown in FIG. 3, housing 10 contains an upper reservoir 20 containing fresh luminol solution. Porous material 12 extends between upper reservoir 20 and lower reservoir 11, and the luminol solution in reservoir 20 flows by wicking or capilliary action into reservoir 11 via porous material 12 and in contact with gas being tested introduced into housing 10 via gas inlet tube 14.

Apparatus of the type shown in FIG. 3 may be designed to operate on the "hourglass" principle, if desired, the apparatus being inverted after all of the luminol solution has passed from reservoir 20 to reservoir 11. The luminol solution then will flow back into reservoir 20 by means of wicking action.

The apparatus of FIG. 3 also may be designed in cartridge form with the two reservoirs, the luminol solution and possibly porous material 12 being replaced as a unit.

An advantage of the FIG. 3 embodiment is that no pump is required to cause the luminol solution to flow. As a consequence, the embodiment of FIG. 3 is capable of being made light and small enough to be easily portable and used by personnel to measure gas exposure levels.

In practising the present invention for detecting the presence of and measuring certain nitrogen-containing gases in a gas sample, a luminol solution free from metal ions flows through a porous material, either as a result of being pumped, or as a result of wicking or capilliary action. The flowing luminol solution is contacted with the gas sample, and the resulting chemiluminescence which occurs when the gas sample contains certain nitrogen gases is detected and measured, the former indicating the presence of the certain nitrogen gases and the latter the concentration thereof.

The concentration of luminol in the luminol solution may be varied. As was reported by Maeda et al (Anal. Chem. 1980, 52, 307), the maximum chemiluminescence was obtained with a luminol concentration in the range $1 \times 10^{-4}$ to $1 \times 10^{-3}$ molar (M) and was essentially independent of luminol concentration within this range.

NaOH may be employed to provide the required alkalinity for the luminol solution. The maximum chemiluminescence was obtained with a NaOH concentration of $5 \times 10^{-2}$M, decreasing by a factor of 4 for a factor of 2 change in the NaOH concentration about this maximum, as previously reported by Kok et al (Environ. Sci. Technol. 1978, 12, 1072).

Deionized or distilled water free of metal ions should be used in the luminol solution.

Interferences due to ozone ($O_3$) can be minimized by addition of $Na_2SO_3$ to the solution. We have found that the maximum increase in the $NO_2/O_3$ response ratio occurs at a $Na_2SO_3$ concentration of between $1 \times 10^{-3}$M and $1 \times 10^{-1}$M. Moreover, we have found that the resulting solution was much more stable with passage of time than a solution of luminol/NaOH which did not contain $Na_2SO_3$.

We also have discovered that the addition of small amounts of one or more alcohols such as, lower alkanols, e.g., methanol, ethanol, propanol, isopropanol, butanol, etc. greatly enhanced the sensitivity and specificity of the apparatus to $NO_2$. For example, the addition of 0.05% (v/v) of methanol increased the response by a factor of 2 and increased the ratio of $NO_2/O_3$ signal response by about the same factor. This discovery is of significance not only with the specific method and apparatus disclosed herein, but also in luminol/$NO_2$ reactions generally.

Tests were made for interferences from other gases. No response was seen when the detector was exposed to 20 parts per billion (ppbv) of each of NO, $NH_3$, $HNO_3$, $CH_3ONO$, HCN or $SO_2$.

The apparatus was found to respond to peroxyacetylnitrate (PAN) with the same sensitivity as for $NO_2$. However, it has been found that passage of the sample gas, e.g., air, through a trap containing $FeSO_4$ or silica gel impregnated with $FeSO_4$ removes the $NO_2$ without affecting PAN. This provides a method for measuring PAN with the apparatus. $NO_2$ can be measured in the presence of PAN from the difference in the signal without the trap (PAN+$NO_2$) and that with the gas passing through the trap (PAN).

The apparatus responds to $O_3$ with a relative sensitivity between some 30 to 300 times less than for $NO_2$ when the luminol solution contains the optimum amount of $Na_2SO_3$ and methanol. We have discovered that the $O_3$ can be removed quantitatively by first passing the gas sample through a trap containing cotton wool or animal hair or a mixture thereof. $NO_2$ in the gas sample was found to pass through this trap with a loss of less than 5%.

The apparatus can be used for measuring $NO_x$ (NO+$NO_2$) and by difference to measure NO. The method involves converting NO to $NO_2$. This can be accomplished by passing the gas sample through a trap filled with 10% by weight chromium oxide ($CrO_3$) on 6-12 mesh silica gel as described by Levaggi et al (Environ. Sci. Technol. 1974, 8, 348). The trap used was an aluminum cylinder 25 cm long and 3.5 cm in diameter with glass wool plugs at both ends to confine the oxidizer. NO is oxidized to $NO_2$ by the $CrO_3$ and is measured as $NO_2$. The amount of NO is obtained by subtracting the signal obtained without the converter ($NO_2$) from that with the converter (NO+$NO_2$). The conversion efficiency of the conversion was found to be 60-70%. The conversion efficiency was found to fluctuate by up to 5% with time, which may be attributed to the effect of sample gas humidity on conversion efficiency as discussed by Levaggi et al in the aforementioned publication. This fluctuation can be eliminated by maintaining the gas sample at a constant relative humidity in excess of the sampled air humidity by incorporation of a constant humidity source to the sampled air stream.

Methyl nitrite, $CH_3ONO$, is not measured on the $NO_2$ channel but is converted to $NO_2$ by the $CrO_3$ converter and therefore is measured as $NO_2$. No other interferences were encountered.

It is also possible to use the instrument as an $NO_y$ (NO+$NO_2$+$HNO_3$+PAN) detector. Passage of the sample gas through a stainless steel tube maintained at a temperature of 500° C. will convert $HNO_3$ to $NO_2$ and NO. In combination with the $FeSO_3$ and $CrO_3$ converters, it is possible to determine the concentration of each of these species separately.

The sensitivity of the instrument to $NO_2$ depends on the condition of the filter paper and the particular solution being used and will change slowly with time. It is therefore necessary to calibrate the instrument at regular intervals (typically once a day in constant use). It is first necessary to remove the $NO_2$ from the gas sample to provide a background reading. This can be accomplished by passing the gas sample through a trap containing $FeSO_2$, which scrubs out the $NO_2$ component. Calibration has then is added through a calibrated $NO_2$ permeation device.

Since the conversion of NO to $NO_2$ is less than 100%, it is necessary to determine the conversion factor. This can be accomplished by adding known quantities of NO to the sample gas from a gas cylinder containing a few ppmv of NO in $N_2$. Permeation devices also can be used to calibrate the system for $HNO_3$.

It has also been shown that it is possible to measure ozone by allowing the ozone to react with nitric oxide added to the intake system. This reaction produces $NO_2$ which is then measured by the luminol detector. The measure of ozone is obtained by a difference technique. Two methods of determining the difference have been demonstrated. One method involves a system whereby the flow of nitric oxide to the intake system is alternately turned on and off, the flow enters into a reaction volume in which the reaction between nitric oxide and the $O_3$ can be shown to proceed to completion. The second method comprises alternately switching in and out of the intake system an ozone-removing trap such as described above. The ability to measure ozone enables one instrument to be used for air monitoring of both $O_3$ and the oxides of nitrogen whereas in the prior art, two instruments were required to measure these components.

Figure 4:
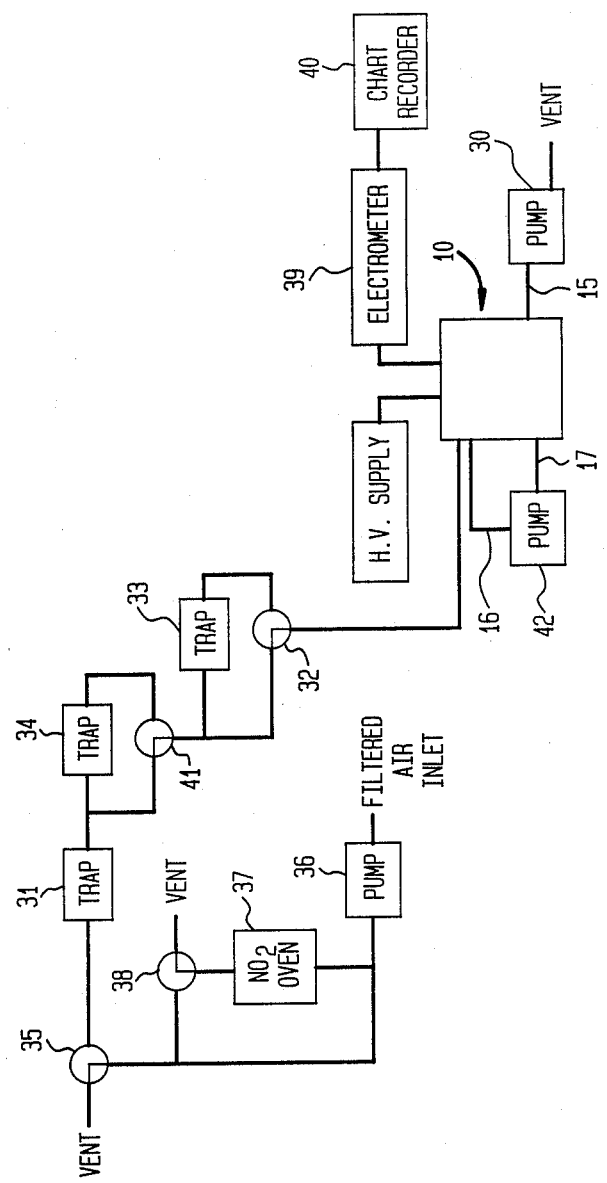
FIG. 4 illustrates additional details of a chemiluminescent instrument embodying the present invention and useful in practising the same.

Referring now to FIG. 4, apparatus of the type shown in FIG. 1, for example is shown at 10 in FIG. 4. A pump 30 pulls sample gas through the system and has its inlet connected to tube 15. A trap 31, whose outlet is connected via valves 41 and 32 to tube 14, contains cotton wool and/or animal hair to remove $O_3$ from the gas sample (air) while letting $NO_2$ through. A trap 33, which is switched into and out of the gas stream by valve 32, contains a $CrO_3$ converter to oxidize NO to $NO_2$. Another trap 34, which can be switched by valve 41 to receive the gas sample from trap 31 or bypassed, contains $FeSO_4$ to remove $NO_2$ from the gas sample without affecting PAN.

The intake is exposed either to calibration gas or zero air (air from which all $NO_2$ has been removed) by valve 35. An auxiliary pump 36 supplies filtered diluent air from which $NO_2$ has been removed. This same filtered air also is passed through a $NO_2$ permeation tube oven 37 and can be added for calibration through valve 38. A pump for the luminol solution is shown at 42.

The light output is detected by a photomultiplier 13 (FIG. 1), e.g., an RCA-1P28 whose photocurrent is measured by a picoammeter 39 and displayed on a chart recorder 40.

While preferred embodiments have been described and illustrated herein, the person skilled in the art will appreciate that changes and modifications may be made therein without departing from the spirit and scope of this invention as defined in the appended claims.

What we claim is:

1. Apparatus for detecting the presence of, and measuring, nitrogen gases in a gas sample, the apparatus comprising:

means defining a reaction region for receiving a gas sample;

a gas inlet positioned and arranged for supplying a gas sample to said means defining a reaction region;

a gas outlet positioned and arranged for removing a gas sample from said means defining a reaction region;

a luminol inlet positioned and arranged for transferring to said means defining a reaction region a luminol solution free from metal ions;

a porous material positioned and arranged to be substantially stationary by stationary support means in said means defining a reaction region, said porous material having a receiving portion thereof positioned in the vicinity of said luminol inlet and arranged to communicate and receive luminol solution from said luminol inlet, said porous material providing a path for the luminol solution to flow therethrough by wicking, in the presence of a gas sample, and providing a surface on which the gas sample reacts with the luminol solution while the luminol solution flows through said path;

a receiving reservoir positioned and arranged for receiving the luminol solution after flowing through said path of said porous material and reacting with the gas sample; and photomultiplier means arranged in the vicinity of said means defining a reaction region, positioned and arranged for detecting and measuring chemiluminescence the luminol solution.

2. Apparatus according to claim 1 wherein said porous material is a filter paper.

3. Apparatus according to claim 1 wherein said porous material is selected from at least one of the group consisting of glass fibres, cellulose fibres, and glass frit.

4. Apparatus according to claim 1 including a trap containing a selectable one of $FeSO_4$ and $FeSO_4$ suspended on silica gel through which said gas sample is passed before contacting the luminol solution, thereby scrubbing $NO_2$ from the gas sample.

5. Apparatus according to claim 1 including a trap containing $CrO_3$ through which the gas sample is passed before contacting the luminol solution, thereby oxidizing NO in the gas sample to $NO_2$.

6. Apparatus according to claim 1 including means for selectably adding nitric oxide at said gas inlet, thereby enabling ozone to be measured.

7. The apparatus of claim 1 wherein there is further provided a supply reservoir coupled to said luminol inlet for receiving and containing a supply of luminol solution, said porous material extending into said supply reservoir for communicating with the supply of luminol solution contained therein.

8. Apparatus according to claim 1 including a trap containing at least one of cotton wool and animal hair through which the gas sample is passed before contacting the luminol solution, thereby scrubbing $O_3$ from the gas sample.

9. Apparatus according to claim 8 including a second trap containing $FeSO_4$ through which the gas sample is passed before contacting the luminol solution, thereby scrubbing $NO_2$ from the gas sample, a third trap containing $CrO_3$ through which the gas sample is passed before contacting the luminol solution, thereby oxidizing NO in the gas sample to $NO_2$, and means for selectively passing and bypassing said traps with the gas sample.

* * * * *